US00PP14498P29

(12) United States Plant Patent
Talmadge

(10) Patent No.: US PP14,498 P2
(45) Date of Patent: Jan. 27, 2004

(54) DIASCIA PLANT NAMED 'BALWHISCRAN'

(50) Latin Name: *Diascia hybrida*
Varietal Denomination: Balwhiscran

(75) Inventor: Paul Talmadge, Guadalupe, CA (US)

(73) Assignee: Pan American Seed, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/329,858

(22) Filed: Dec. 26, 2002

(51) Int. Cl.[7] ..... A01H 5/00
(52) U.S. Cl. ..... Plt./263
(58) Field of Search ..... Plt./263

*Primary Examiner*—Anne Marie Grunberg
(74) *Attorney, Agent, or Firm*—Wood, Phillips, Katz, Clark & Mortimer

(57) ABSTRACT

A new and distinct Diascia plant named 'Balwhiscran' characterized by its deep red colored flowers, spreading, trailing growth habit, and medium green foliage.

2 Drawing Sheets

Latin name of genus and species of plant claimed: Diascia hybrida.
Variety denomination: 'Balwhiscran'.

BACKGROUND OF INVENTION

The present invention comprises a new and distinct Diascia plant, botanically known as Diascia hybrida, and hereinafter referred to by the cultivar name 'Balwhiscran'.

The new cultivar was developed by the inventor in a controlled breeding program during February 1999, at Guadalupe, Calif. The objective of the breeding program was the development of Diascia cultivars with a well-branched, spreading growth habit, continuous flowering and medium green foliage.

The female (seed) parent of 'Balwhiscran' was the proprietary *Diascia barberae* selection designated 399-1 (nonpatented),characterized by its flowers of a deep red color, large leaves of a light green color and spreading habit. The male (pollen) parent of 'Balwhiscran' was the proprietary *Diascia mollis* selection designated 391-5 (nonpatented), characterized by its flowers of a pink color, small leaves of a dark green color and upright growth habit. 'Balwhiscran' was discovered and selected in June 1999 as a single flowering plant from within the progeny of the above stated cross and was designated 584-4m-7-2.

Asexual reproduction of the new cultivar at Guadalupe, Calif. and West Chicago, Ill. was carried out by the use of terminal stem cuttings and has demonstrated that the characteristics of the new cultivar as herein described are firmly fixed and retained through successive generations of such asexual propagation.

SUMMARY OF INVENTION

It was found that the cultivar of the present invention:

(a) exhibits deep red colored flowers, (b) forms foliage of a medium green color, and (c) exhibits a spreading and, trailing growth habit.

The new cultivar can be compared to the commercially available Diascia variety, 'Red Ace'. In side-by-side comparison, plants of the new cultivar are taller and narrower, and have lighter pink flowers than those of 'Red Ace'.

BRIEF DESCRIPTION OF PHOTOGRAPH

The accompanying photographs show as nearly true as it is reasonably possible to make the same in color illustrations of this type, typical flower and foliage characteristics of the new cultivar. The plants were grown for 11 weeks in a greenhouse at West Chicago, Ill.

DETAILED BOTANICAL DESCRIPTION

Figure 1:
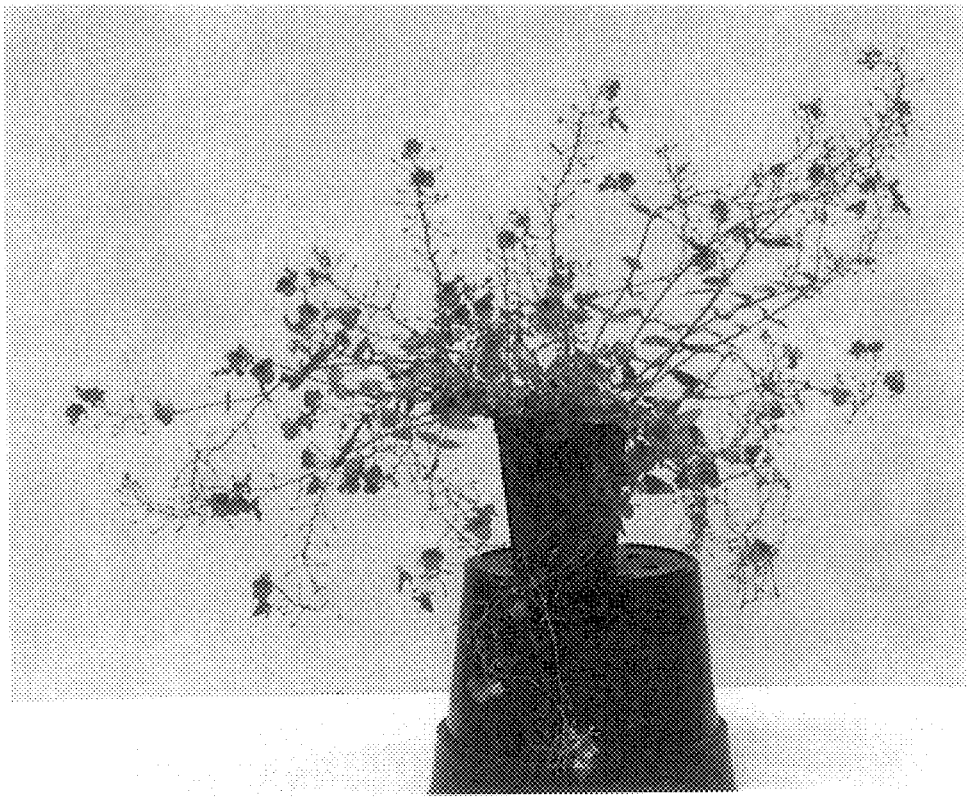
FIG. 1 illustrates the overall growth habit of the new cultivar.
Figure 2:
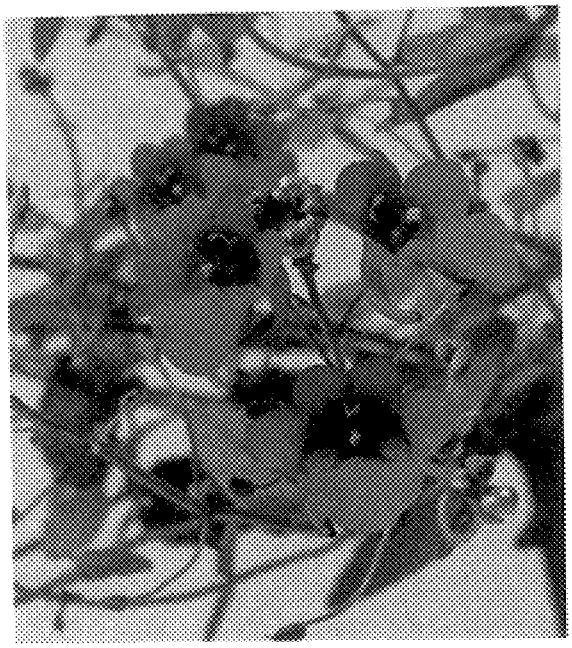
FIG. 2 illustrates a close up view of individual flowers of the new cultivar.

The new cultivar has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Apr. 26, 2002. The readings were taken between 1:00 and 3:00 p.m. under natural daylight conditions. The plants were produced from cuttings taken from stock plants and were grown in a double polycarbonate covered greenhouse under conditions comparable to those used in commercial practice. The plants were grown for 9 weeks while utilizing a soilless growth medium and maintaining temperatures of approximately 62° to 75° F. (17° to 24° C.) during the day and approximately 52° to 60° F. (11° to 15° C.) during the night and light levels of 5,000 to 8,000 footcandles.

Classification: Botanical — Diascia hybrida cultivar 'Balwhiscran'.

Parentage:

*Female parent.*—Proprietary *Diascia barberae* selection 399-1.

*Male parent.*—Proprietary *Diascia mollis* selection 391-5.

Propagation:

*Type cutting.*—Terminal tip.

*Time to initiate roots.*—Approximately 14 to 21 days.

*Root description.*—Fibrous, branching.

Plant description:

*Crop time.*—Approximately 5 to 7 weeks from planting of rooted cuttings in a 10 cm pot.

*Habit of growth.*—Vigorous. Pinching improves branching. A mature plant, 9 weeks after the planting of a rooted cutting, measures approximately 28.8 cm in height and approximately 63.3 cm in width with approximately 3 main branches and 45 lateral flowering branches.

*Form.*—Spreading, trailing.

*Lateral branch.*—Shape: Square. Length: Approximately 21 cm. Diameter: Approximately 2 mm. Texture: Glabrous. Internode length between leaves: Internode length between flowers: . Color: N144C with overlay of 59A.

*Foliage.*—Type: Simple. Arrangement: Opposite. Shape: Ovate. Margin: Serrate-cilliate. Apex: Acute. Base: Cordate. Texture: Quantity per lateral branch: Approximately 10.2. Leaf length: Approximately 2.6 cm. Leaf width: Approximately 1.7 cm. Leaf orientation to stem: Obtuse to parallel. Leaf fragrance: None. Upper surface of mature foliage is 137A and lower surface is 137B. Upper and lower surfaces have pinnate venation of 138B. Petiole length: Approximately 5 mm. Petiole diameter: Approximately 2 mm. Petiole color: 72B. Upper and lower surfaces of petiole are glabrous.

Flowering description:

*Flowering habit.*—Freely flowering.

*Natural flowering season.*—Year round in greenhouse environment and spring through autumn in outdoor garden.

*Flower arrangement.*—Terminal racemes.

Flower description:

*Type.*—Solitary, five lobed and zygomorphic.

*Fragrance.*—None.

*Aspect.*—Concave.

*Corolla.*—Width: Approximately 1.7 cm. Length: Approximately 1.9 cm. Depth: Approximately 4 mm.

*Petals.*—Number: Five, fused at base. Aspect: Cupped. Two upper petals: Length is approximately 4 mm, width is approximately 5 mm. Lateral petals: Length is approximately 6 mm, width is approximately 6 mm. Sharply curved nectar spurs form at base of each of the lateral petals. Nectar spur length: 5 mm. Nectar spur color: 60C. Lower petal: Length is approximately 1.2 cm, width is approximately 1.2 cm. All petals: Margin: Entire. Apex: Obtuse. Texture: Glabrous and iridescent. Color: Upper surface is closest to 54A. Lower surface is closest to 54B. Indentation at base of upper petals is 12A.

*Sepals.*—Quantity: 5. Shape: Lanceolate. Length: Approximately 3 mm. Width: Approximately 1 mm. Apex: Acute. Margin: Entire. Upper surface of sepals is moderatly pubescent. Lower surface has no pubescence. Upper and lower surfaces are 143C. Calyx shape: Star. Calyx length: Approximately 3 mm. Calyx diameter: Approximately 5 mm.

*Pedicel.*—Length: Approximately 1.5 cm. Texture: Densely pubescent. Color: 143C.

*Peduncle.*—Length: Approximately 5.1 cm. Diameter: Approximately 1 mm. Aspect: At acute angle to branch. Texture: Moderately pubescent. Color: 143C.

*Bud.*—Shape: Oval, flat. Length: Approximately 4 mm in length. Diameter: Approximately 6 mm. Color: 54B.

*Reproductive organs.*—Androecium: There are 3 stamens. Anther shape: Square. Anther length: 1 mm. Anther color: 12B. Pollen is abundant and 12A in color. Gynoecium: There is one pistil, 3 mm in length. Stigma shape: Round. Stigma length: Less than 1 mm. Stigma color: 145A. Style length: Approximately 2 mm. Style color: N144D with overlay of 72B in center. Ovary length: Approximately 1.5 mm. Ovary color: N144C.

Seed production: Seed production has not been observed.

Disease resistance: Resistance to pathogens has not been observed.

Hardiness zone: 'Balwhiscran' is hardy in zones nine (9) and above.

I claim:

1. A new and distinct Diascia hybrida plant named 'Balwhiscran' substantially as herein shown and described, which:

(a) exhibits deep red colored flowers, (b) forms medium green foliage, and (c) exhibits a spreading and trailing growth habit.

* * * * *